United States Patent [19]

Sulzbach et al.

[11] 4,137,055

[45] Jan. 30, 1979

[54] PROCESS FOR SEPARATING TETRAFLUOROETHYLENE FROM NITROGEN AND CARBON MONOXIDE

[75] Inventors: Reinhard A. Sulzbach, Burghausen, Salzach; Georg Oberauer, Burgkirchen, Alz, both of Fed. Rep. of Germany

[73] Assignee: Hoechst Aktiengesellschaft, Frankfurt am Main, Fed. Rep. of Germany

[21] Appl. No.: 827,104

[22] Filed: Aug. 23, 1977

[30] Foreign Application Priority Data

Aug. 27, 1976 [DE] Fed. Rep. of Germany ....... 2638650

[51] Int. Cl.² .............................................. B01D 19/00
[52] U.S. Cl. ..................................... 55/71; 260/653.3
[58] Field of Search ........................... 55/71; 260/653.3

[56] References Cited

U.S. PATENT DOCUMENTS

| | | |
|---|---|---|
| 3,221,070 | 11/1965 | Okamura et al. ................. 260/653.3 |
| 3,347,021 | 10/1967 | Hutton ..................................... 55/71 |
| 3,680,289 | 8/1972 | Werner et al. ........................... 55/71 |

FOREIGN PATENT DOCUMENTS 866002  4/1961  United Kingdom ......................... 55/71

*Primary Examiner*—Bernard Nozick
*Attorney, Agent, or Firm*—Connolly and Hutz

[57] ABSTRACT

Tetrafluoroethylene, often obtained in industrial processes in admixture with nitrogen and/or carbon monoxide can be separated practically quantitatively by absorption in aliphatic hydrocarbons or aliphatic ketones boiling at a temperature in the range of from +50 to +130° C at atmospheric pressure with subsequent desorption. A separation from three component mixtures is also possible. Components boiling at a temperature below the boiling point of tetrafluoroethylene, which are absorbed together with the tetrafluoroethylene, can be separated by known methods.

3 Claims, 1 Drawing Figure

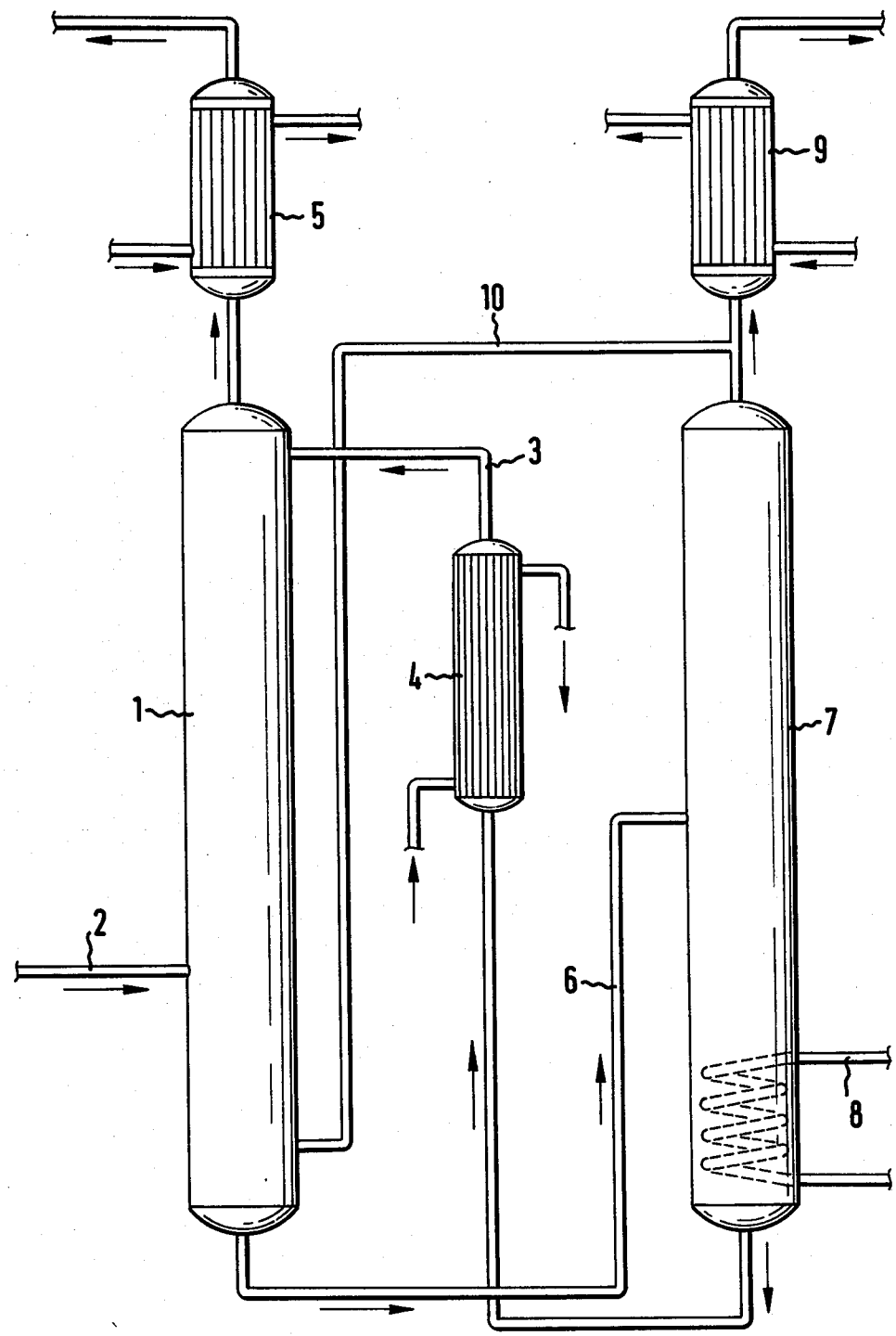

PROCESS FOR SEPARATING TETRAFLUOROETHYLENE FROM NITROGEN AND CARBON MONOXIDE

This invention relates to a process for separating tetrafluoroethylene from gas mixtures containing nitrogen, carbon monoxide or mixtures of the two gases in addition to tetrafluoroethylene.

In the industrial production of tetrafluoroethylene as well as in the polymerization of tetrafluoroethylene gas mixtures are obtained which contain tetrafluoroethylene in admixture with nitrogen, carbon monoxide or with mixtures thereof and from which it must be separated and recovered.

Large amounts of nitrogen in the gas mixture are to be expected when the polymerization reactors used for the manufacture of polytetrafluoroethylene are scavenged with nitrogen to remove atmospheric oxygen and then with tetrafluoroethylene, or when tetrafluoroethylene is produced by pyrolysis of fluorocarbon, fluorohydrocarbon or fluorohalohydrocarbon compounds in the presence of nitrogen as inert diluent. Furthermore, nitrogen is contained in the gases at the beginning of the tetrafluoroethylene production when the pyrolysis furnace or other apparatus have previously been scavenged with nitrogen.

Carbon monoxide is formed as gaseous by-product when fluorocarbons, fluorohydrocarbons, or fluorohalohydrocarbons are pyrolyzed in the presence of steam for the production of tetrafluoroethylene.

Gas mixtures consisting of nitrogen, carbon monoxide and tetrafluoroethylene, which may also contain a minor proportion of fluorinated compounds having a boiling point below that of tetrafluoroethylene, are formed when the scavenging gas of the polymerization reactors and the pyrolysis gas from the tetrafluoroethylene production, from which HCl has been separated, are mixed and the mixture is worked up by distillation.

If pure tetrafluoroethylene shall be obtained from gas mixtures by fractional distillation, the components to be separated must first be liquefied.

When the tetrafluoroethylene-containing gas mixture to be liquefied does not contain any components having a boiling point considerably below that of tetrafluoroethylene, the liquefaction is suitably carried out without the application of pressure at a temperature of about $-80°$ C. The application of pressure for the liquefaction is not advisable because of the tendency to explode of tetrafluoroethylene.

If, however, the tetrafluoroethylene-containing gas mixture to be liquefied contains components boiling at a temperature essentially below the boiling point of tetrafluoroethylene ($-76.3°$ C. under 1.01 bar) the liquefaction becomes rather difficult. This is the case with gas mixtures containing nitrogen and/or carbon monoxide. To liquefy these components temperatures are required which are unacceptable in industry for economical considerations.

The liquefaction of a gas mixture consisting of tetrafluoroethylene and nitrogen or carbon monoxide or mixtures of the two latter compounds, which gas mixture may further contain other fluorine-containing compounds boiling at a temperature above or below the boiling point of tetrafluoroethylene under the conditions suitable for the liquefaction of tetrafluoroethylene (about $-80°$ C, without the application of pressure), yields a gas current which cannot be liquefied and essentially consists of nitrogen, carbon monoxide or mixtures thereof and tetrafluoroethylene entrained according to its partial pressure. According to its vapor pressure (0.820 bar at $-80°$ C.) the tetrafluoroethylene is contained in the non liquefiable gas current in a proportion of 45% by volume.

The recovery of tetrafluoroethylene from gas mixtures containing same in admixture with nitrogen and carbon monoxide is absolutely necessary because, on the one hand, tetrafluoroethylene is an extremely expensive substance, the quantitative recovery of which is desirable from an economical point of view, and, on the other, it is toxic and, therefore, cannot be let off into the atmosphere for reasons of environmental protection.

To avoid losses of tetrafluoroethylene it has repeatedly been pointed out that the pyrolytic production of tetrafluoroethylene should not be carried out in the presence of inert gases such as nitrogen (cf. DT-AS 1,073,475 and DT-AS 1,222,040).

Published Japanese patent specification Sho 48-10444 relates to a process for isolating and recovering tetrafluoroethylene from a gas mixture containing same in admixture with low boiling components, i.e. by-products formed in the pyrolysis of difluorochloromethane in the presence of steam such as various low boiling fluorine-containing organic compounds, for example trifluoromethane, vinylidene fluoride or hexafluoroethane, in addition to carbon monoxide. In this process the first runnings of the distillation, consisting of tetrafluoroethylene and the low boiling components, is contacted at elevated pressure with a liquid perhalogen hydrocarbon which selectively absorbs the tetrafluoroethylene and from which it is then liberated by pressure release. An essential drawback of this process resides in the fact that the absorption of tetrafluoroethylene in the liquid perhalohydrocarbon must be carried out under pressure. It is known that tetrafluoroethylene under pressure may decompose with explosion into carbon and tetrafluoromethane. Parts of the production plant operated under a tetrafluoroethylene pressure above 5 bars must, therefore, comply with severe safety specifications.

Consequently, it has been desirable to find a process according to which tetrafluoroethylene contained in highly varying proportions in gas mixtures of the aforesaid type, besides nitrogen or carbon monoxide, can be recovered as quantitatively as possible and in economic manner without the application of high excess pressure.

The present invention provides a process for separating tetrafluoroethylene from gas mixtures containing, in addition to tetrafluoroethylene, nitrogen, carbon monoxide or mixtures of the two latter gases and possibly other components having a lower boiling point than tetrafluoroethylene and originating from the tetrafluoroethylene production, which comprises contacting the gas mixture with a saturated aliphatic ketone, a saturated aliphatic hydrocarbon or a mixture thereof having a boiling point in the range of from 50° C. to 130° C., allowing the nitrogen and/or carbon monoxide to escape in gaseous form, absorbing the tetrafluoroethylene, possibly together with the other components boiling at a temperature below the boiling point of tetrafluoroethylene in the ketone and/or hydrocarbon, liberating the tetrafluoroethylene and possibly the other components from the charged absorption agent by heating to its boiling point and optionally separating tetrafluoroethylene from the other components having a boiling point below that of tetrafluoroethylene by known methods.

The gas mixtures to be separated by the process of the invention can be two component mixtures of tetrafluoroethylene with nitrogen or with carbon monoxide or three-component mixtures of the said gases. The two- or three-component mixtures may additionally contain further components having a boiling point below that of tetrafluoroethylene, such as fluorine-containing oganic by-products, for example trifluoromethane, difluoromethane, hexafluoroethane and vinylidene fluoride, formed in the pyrolysis of fluorocarbons, fluorohydrocarbons or fluorohalohydrocarbons, for example of difluorochloromethane, and optionally also a little carbon dioxide.

The process of the invention is preferably carried out in continuous manner as follows: the gas mixture to be separated is introduced into the lower part of an absorption column. In the absorption column, which may be a packed column or a bubble tray column, the liquid absorption agent flows in downward direction. At the head of the absorption column nitrogen or carbon monoxide or the mixture thereof, which have an extremely low solubility in the absorption agent, is withdrawn, while the solution of tetrafluoroethylene in the absorption medium is discharged at the bottom of the column.

The absorption medium charged with tetrafluoroethylene and leaving the absorption column is passed into a second column provided with heating means in the lower section. In said column the absorption medium is heated to boil whereby the dissolved tetrafluoroethylene escapes together with the other dissolved low boiling components, if any. The desorbed components are withdrawn at the head of the column. The degassed absorption medium is then cooled to the desired absorption temperature, whereupon it can be introduced again at the head of the absorption column.

The absorption is preferably carried out at a temperature of from $-30°$ C. to $+30°$ C., more preferably $+10°$ C. to $+25°$ C. Absorption and desorption can be carried out at the same pressure. The pressure applied is not critical, low pressure, atmospheric pressure as well as elevated pressure being possible. The special advantage of the process of the invention resides in the fact that high excess pressure need not be applied and that, therefore, an explosion like decomposition of tetrafluoroethylene is excluded. The process is suitably carried out in a pressure range of from 1 to 3 bars, atmospheric pressure being preferred.

Suitable absorption media in the process of the invention are aliphatic saturated ketones and aliphatic saturated hydrocarbons. The absorption medium should have a boiling point in the range of from $+50°$ to $+130°$ C., preferably $+50°$ to $+90°$ C., since in a continuous process such a temperature range is the most favorable one as regards energy efficiency. Moreover, the absorption agent should have a freezing point below $-40°$ C., preferably below $-75°$ C., so that in the condensers mounted on the columns of the desorption plant and serving to reduce the partial pressure of the absorption medium or in the liquefaction of the recovered tetrafluoroethylene a deposition of solids does not occur. Under the absorption and desorption conditions the absorption agent should be thermally and chemically stable. The ratio of the solubility of nitrogen or of carbon monoxide to the solubility of tetrafluoroethylene in the absorption medium should be at least 1:5, preferably above 1:10.

Under these conditions aliphatic saturated ketones having from 3 to 6 carbon atoms or mixtures thereof proved to be especially advantageous. There are mentioned by way of example methylethyl ketone, methylisopropyl ketone, diethyl ketone, methylisobutyl ketone and preferably acetone. Aliphatic saturated hydrocarbons having from 6 to 8 carbon atoms in a straight or branched chain are also very suitable, for example n-hexane, n-heptane, 2-methyl-pentane, n-octane and isooctane. The hydrocarbons having 6 to 8 carbon atoms can also be used in the form of mixtures, possibly of their isomers. Especially good results are obtained with gasoline fractions having a boiling point or range within the aforesaid limits. Mixtures of the said ketones and hydrocarbons can also be used.

The amount of absorption medium to be circulated can be varied within wide limits, but care should be taken that it is present in an amount which corresponds at least to the solubility of tetrafluoroethylene therein. In practice, it proved advantageous to use an excess, that is to say an amount of absorption agent above the lower limit defined by the solubility of tetrafluoroethylene at the temperature used and the pressure applied in each case, in other words 1.1 to 10 times the amount of absorption agent, 1.1 to 3 times the amount with respect to the solubility of tetrafluoroethylene being preferred. This corresponds under normal conditions and depending on the type of absorption medium used to about 0.5 to 20 liters per liter of gaseous tetrafluoroethylene in the starting mixture.

In the following Table I are indicated the proportion of solubility, defined by gas chromatography, of nitrogen to tetrafluoroethylene for some absorbents especially suitable in the process of the invention and their boiling points and freezing points.

The solubilities of carbon monoxide and of nitrogen are practically equal in the solvents to be used in the process of the invention, at 20° C. and 740 torrs they are in the range of from 0.1 to 0.2 liter of gas per liter of absorbent. These accidentally identical solubility properties of $N_2$ and CO in the aforesaid absorbents make possible the selective separation of tetrafluoroethylene from three component mixtures consisting of nitrogen, carbon monoxide and tetrafluoroethylene in one operation.

Table I

| absorbent | solubility ratio of $N_2$ : TFE at 20° C and 740 torrs | boiling p. [° C] | freezing p. [° C] |
|---|---|---|---|
| acetone | 1 : 15.7 | 56.2 | − 95 |
| methylethyl ketone | 1 : 20.5 | 79.6 | − 87 |
| methylisopropyl ketone | 1 : 5.0 | 95 | − 92 |
| diethyl ketone | 1 : 20.2 | 102.7 | − 42 |
| methylisobutyl ketone | 1 : 11.0 | 116.8 | − 84.7 |
| n-hexane | 1 : 12.0 | 68 | − 95 |
| n-octane | 1 : 20.5 | 125 | − 56.5 |
| gasoline (boiling range 80 - 100° C) | 1 : 9.5 | 80 - 110 | — |
| iso-octane | 1 : 13.0 | 99.2 | − 107 |

When the gas mixture to be separated by the process of the invention contains, besides nitrogen, carbon monoxide or mixtures thereof and tetrafluoroethylene, further components of the aforesaid type having a boiling point below that of tetrafluoroethylene, as obtained in the pyrolysis for the manufacture of tetrafluoroethylene, said components are absorbed in the absorption medium together with tetrafluoroethylene and then desorbed with tetrafluoroethylene. Tetrafluoroethylene can be separated from said components by known methods, for example in a low temperature distillation plant as belongs in most cases to an industrial plant for the production of tetrafluoroethylene, or by a usual method of extractive distillation.

The following examples illustrate the invention, the numerals 1 to 10 referring to the accompanying drawing of the reaction apparatus.

EXAMPLE 1

1.2 m³/hr of a gas mixture consisting of 26% by volume of nitrogen and 74% by volume of tetrafluoroethylene were introduced through conduit (2) into an absorption column (1) having a diameter of 20 cm and a height of 8 m, which column was filled with filling bodies (Pall rings, diameter 15 mm). At the head the absorption column was fed through conduit (3) with 750 kg/hr of acetone which had been cooled to +20° C. in cooler (4). Via condenser (5), operated with methanol cooled to −45° C., 311 l/hr of pure nitrogen escaped. In the upper section of absorption column (1) a temperature of 24° C. prevailed while in the lower section the temperature was 22° C.

The acetone charged with tetrafluoroethylene leaving column (1) at the lower end was passed through conduit (6) into desorption column (7) which had the same dimensions and filling as column (1) and was heated in the lower section by a coil (8) operated with steam. In the column the following temperatures prevailed; in the sump 70° C., in the center 61° C. and at the head 55° C. From the condenser (9), operated with methanol cooled to −45° C., 889 l/hr of tetrafluoroethylene containing 0.1% by volume of nitrogen were discharged.

The absorption and the desorption were carried out at a pressure of 1.4 bars (i.e. 0.4 bar above atmospheric). The absorption column and the desorption column were connected with each other by a conduit (10) for pressure compensation.

EXAMPLE 2

Under the conditions of Example 1 the absorption column was charged with 1.2 m³/hr of a gas mixture of the following composition:
29.5% by volume of nitrogen
19.1% by volume of carbon monoxide
43.3% by volume of tetrafluoroethylene
2.0% by volume of vinylidene fluoride
3.7% by volume of trifluoromethane
0.6% by volume of difluoroemethane
0.2% by volume of difluorochloromethane
1.6% by volume of carbon dioxide A gas of this composition is obtained in the liquefaction of a tetrafluoroethylene-containing gas mixture at about −80° C. in the form of a non condensable gas current. For liquefaction a pyrolysis gas obtained by thermolysis of difluorochloromethane was used together with a mixture of nitrogen and tetrafluoroethylene obtained in the polymerization of tetrafluoroethylene.

The separation was carried out as described in Example 1 using acetone as absorption medium.

At the head of the absorption column 583 l/hr of a gas mixture composed of
60.7% by volume of nitrogen
39.2% by volume of carbon monoxide and
0.03% by volume of tetrafluoroethylene escaped.

After desorption, there was obtained from the desorption column a gas mixture consisting of
0.06% by volume of nitrogen and carbon monoxide
84.2% by volume of tetrafluoroethylene
3.9% by volume of vinylidene fluoride
7.2% by volume of trifluoromethane
1.1% by volume of difluoromethane
0.4% by volume of difluorochloromethane and
3.1% by volume of carbon dioxide.

The impurities contained in the gas mixture were separated in a series-connected, continuously operated low temperature distillation column under a pressure of 3 bars. In the sump of the column 473 l/hr of pure tetrafluoroethylene were obtained, while at the head 144 l/hr of a gas mixture consisting of the aforesaid components having a lower boiling point than tetrafluoroethylene and 32% by volume of tetrafluoroethylene were discharged. The amount of tetrafluoroethylene corresponds to 9% of the amount obtained from the desorption column.

EXAMPLE 3

Under the conditions of Example 1, the absorption column was fed with 1.2 m³/hr of a gas mixture consisting of 55% by volume of nitrogen and 45% by volume of tetrafluoroethylene.

At the head of the absorption column 750 kg/hr of n-hexane were introduced instead of acetone. At the head of the absorption column 660 l/hr of nitrogen containing 0.02% of tetrafluoroethylene were obtained and after desorption 540 l/hr of pure tetrafluoroethylene were obtained from the desorption column.

What is claimed is:

1. A process for separating tetrafluoroethylene from a gaseous mixture containing, in addition to tetrafluoroethylene, a member of the group consisting of nitrogen, carbon monoxide and mixtures thereof, which comprises contacting said gaseous mixture with a liquid absorption medium selected from the group consisting of saturated aliphatic ketones containing 3 to 6 carbon atoms and mixtures thereof having a boiling point in the range of from +50° C. to +130° C., and being present in an amount of from 0.5 to 20 liters per liter of tetrafluoroethylene in said gaseous mixture, whereby absorbing the tetrafluoroethylene in said absorption medium, separating and removing said member, and then heating said absorption medium to its boiling point whereby the tetrafluoroethylene is recovered.

2. The process of claim 1, wherein the liquid absorption medium is acetone.

3. The process of claim 1, wherein said gaseous mixture contains in addition to said member compounds of lower boiling points than that of tetrafluoroethylene which are found in pyrolysis of fluorinated hydrocarbons and said compounds being absorbed and recovered together with the tetrafluoroethylene and subsequently separated therefrom.

* * * * *